United States Patent [19]

McLaughlin

[11] 3,976,588

[45] Aug. 24, 1976

[54] DETERGENTS PROVIDING FASTER DRYING OF CLEANSED SUBSTRATES

[75] Inventor: James Hugh McLaughlin, Chatham, Mass.

[73] Assignee: Center for New Product Development, New York, N.Y.

[22] Filed: Jan. 14, 1975

[21] Appl. No.: 540,993

[52] U.S. Cl.................................. 252/117; 252/120; 252/121; 252/124; 252/125; 252/129; 252/130; 252/133; 252/154; 252/155; 252/173; 252/DIG. 13; 252/DIG. 14; 424/70
[51] Int. Cl.²...................... A61K 7/08; C11D 3/20; C11D 9/26; D06L 1/12
[58] Field of Search............ 252/8.6, 117, 124, 125, 252/129, 130, 121, 133, 542, 154, 155, 173, DIG. 13, DIG. 14; 8/115.6, 127.51; 106/243; 424/70

[56] References Cited
UNITED STATES PATENTS

| | | | |
|---|---|---|---|
| 1,385,854 | 7/1921 | Alexander | 427/337 |
| 1,992,692 | 2/1935 | Englund | 252/115 |
| 2,519,062 | 8/1950 | Miskel | 252/550 |
| 2,660,567 | 11/1953 | Cunder | 106/243 X |
| 2,660,568 | 11/1953 | Cunder | 106/243 X |
| 2,838,422 | 6/1958 | Orthner | 106/243 X |
| 3,008,905 | 11/1961 | Wedell | 252/550 X |
| 3,723,360 | 3/1973 | Hewitt | 252/542 |
| 3,759,846 | 9/1973 | MacDonald | 252/527 |

FOREIGN PATENTS OR APPLICATIONS

| | | |
|---|---|---|
| 857,689 | 1/1961 | United Kingdom |
| 904,262 | 8/1962 | United Kingdom |
| 1,049,063 | 11/1966 | United Kingdom.................. 424/78 |
| 1,268,636 | 3/1972 | United Kingdom.................. 424/70 |

OTHER PUBLICATIONS

*The Chemical Formulary* vol. XIII, Edited by H. Bennett, Chemical Publishing Co., New York, 1967, pp. 404–405.

*Primary Examiner*—Dennis L. Albrecht

[57] ABSTRACT

A detergent composition which is characterized by a faster drying rate for the cleansed substrate and which consists essentially of a cleansing proportion of a water soluble, foaming, non-cationic, organic detergent and an aluminum soap containing from 12 to 18 carbon atoms, the weight ratio of detergent to soap being from about 40:1 to 1:4. Preferred detergent compositions for cleaning hair contain an alkyl sulfate detergent in admixture with either a water soluble soap or an imidazoline detergent in an aqueous medium which further includes a waxy material such as carnauba wax. Preferred detergent compositions for cleansing natural or synthetic fibrous materials contain an anionic or nonionic detergent and a water soluble inorganic or organic builder salt in addition to the aluminum soap.

8 Claims, No Drawings

DETERGENTS PROVIDING FASTER DRYING OF CLEANSED SUBSTRATES

This invention relates to detergent compositions which are characterized by faster wet substrate drying rates. More specifically, this invention relates to compositions for cleaning hair and natural or synthetic fibrous materials containing a detersive proportion of a water soluble, foaming, non-cationic, organic detergent and an aluminum soap having 12 to 18 carbon atoms, the weight ratio of detergent to soap being from about 40:1 to 1:4.

BACKGROUND OF THE INVENTION

To date, research on detergent compositions has been directed toward achieving improved foaming, improved cleansing, and/or improved properties in the cleansed substrate such as luster, manageability and/or antidandruff effects in the hair. Similarly, research on detergent compositions for cleaning natural and synthetic textiles has been directed toward achieving a desired high, low or moderate foam height and improved effects in the cleansed textile such as whiteness or hand. However, little effort has been directed toward the area of drying the cleansed substrate. The drying area is particularly significant at the present time in view of the energy crisis and the consequent need to reduce energy consumption. Textile drying is usually accomplished in an electric or gas dryer or by hanging on an outdoor line and hair drying is generally achieved by manual manipulation of the hair and scalp with a towel or by employing a hair dryer to pass heated air over or through the cleansed, wet hair. In view of the need to reduce energy usage and the desirability of reducing the time required for drying hair and textiles, a need exists for a detergent composition designed to shorten the time and to reduce the energy required for the drying of the wet, cleansed substrates. To date, no detergent composition is available that enables shampooed hair and wet, cleansed textiles to dry more quickly.

SUMMARY OF THE INVENTION

It has now been discovered that detergent compositions characterized by a faster drying rate for the cleansed substrate in its wet state consist essentially of a cleansing proportion of a water soluble, foaming, non-cationic, organic detergent and an aluminum soap containing from 12 to 18 carbon atoms, the weight ratio of detergent to soap being from 40:1 to 1:4.

Preferred hair cleansing compositions contain about 10 to 40% by weight of the organic detergent and 0.5 to 10% by weight of aluminum soap in an aqueous medium which optionally contains up to 15% by weight of a $C_2 - C_3$ alkanol and up to 3% by weight of a waxy material. Such compositions containing the optional components have been found to possess good stability. In addition to imparting faster drying properties to the wet hair, these compositions are effective to cleanse and condition the hair. The conditioning effects leave the hair soft and more manageable, thereby facilitating combing. Also, the hair exhibits less static charge and has a desirable luster.

Preferred compositions for cleansing natural and synthetic textile fabrics contain 5 to 50% by weight of organic detergent in combination with about 2.5 to 50% by weight of aluminum soap, the weight ratio of detergent to aluminum soap being in the range of 5:1 to about 1:2, with the balance being a water soluble detergent builder salt selected from the group of organic and inorganic builder salts in a ratio of about 1 – 10 parts of builder per part of detergent.

While the explanation for the fast drying properties of the inventive detergent compositions is not known, it is thought that the properties are due to the combination of the water soluble detergent and the water-insoluble metallic aluminum soap. It is believed that this combination of ingredients coacts with the substrate in the aqueous detergent solution to reduce the amount of water swelling of the substrate being cleaned during the cleansing operation. In this way less water is thought to be picked up by the substrate during cleansing and, therefore, less water has to be removed during drying which is reflected by a shortened drying time or a drying rate which is faster than usual.

The detergent compositions of this invention may be formulated in the form of a powder, gel or liquid lotion without the need for additional expensive ingredients. Thus, the problems associated with the incorporation of such additional ingredients are eliminated. For example, the need for additional conditioning agents such as gums and oils in hair and textile cleaning compositions and the instability problems attendant to the incorporation of such materials are eliminated. Similarly, the need for substantial proportions of organic, non-aqueous, solvent coupling agents in hair shampoos which cause the hair to become dry and brittle is minimized. Accordingly, the inventive detergent compositions particularly provide flexibility in the formulation of hair cleaning shampoos that simultaneously cleanse the hair and scalp and impart improved manageability to the hair in addition to decreasing the time required for drying the wet hair.

DETAILED DESCRIPTION OF THE INVENTION

The detergent compositions generally described above and in all their embodiments are a discretely balanced mixture of ingredients, each ingredient present contributing to the overall result. In the practice of this invention, the mixture of ingredients is tailored to produce a cleansing detergent composition which produces the desired end result, that is, quicker drying of the wet, cleansed substrate.

It has been discovered that detergent composition resulting in quicker and shorter drying times for hair can be produced by the addition of an effective amount of an aluminum soap to a typical detergent composition which normally comprises a cleansing proportion of a water soluble, foaming, non-cationic, organic detergent, with the weight ratio of detergent to soap being in the range of 40:1 to 1:4, preferably about 15:1 to 4:1 for hair cleansing compositions and about 5:1 to about 1:3 for textile cleansing compositions. Generally, the proportion of the detergent ingredient will be about 5 to 50% by weight of the final composition. Aluminum soap usually is present in liquid hair cleaning compositions in amounts ranging from about 0.5 to about 10% by weight of the total composition and in powder textile cleaning compositions in amounts of about 2.5 to 50% by weight of the total composition. While the amount of aluminum soap is not narrowly critical, it has been found that the specific ranges disclosed above are effective. For example, if lesser amounts of aluminum soap are employed, the improvement in drying rate is not apparent. On the other hand, more than the stated maximum proportions does not result in further increased drying rates.

The aluminum soaps which may be employed in the present invention are the aluminum salts of alkanoic acids having 12 to 18 carbon atoms. The alkanoic acid may be saturated or unsaturated and suitable alkanoic acids include stearic acid, palmitic acid, lauric acid, myristic acid, oleic acid and ricinoleic acid. Usually, the alkanoic acids are commercial grade materials and are obtained from animal and vegetable fats such as tallow and conconut oil. (The distribution of fatty acids in tallow is 24% stearic, 25% palmitic, 42% oleic and 2% linoleic and the distribution of fatty acids in coconut oil is 15% caproic and capric, 48% lauric, 18% myristic, 9% palmitic, and 2% stearic.) Synthetic alkanoic acids also may be employed. Further, the aluminum soaps may be used in their fully neutralized (tri) and partially neutralized (mono- and di-) forms. The preferred soaps are aluminum stearate, aluminum oleate and aluminum ricinoleate, with either fully neutralized or partially neutralized aluminum stearate being most preferred. The aluminum stearates are mineral oil soluble white powders having a specific gravity of about 1.01 and a melting point above about 212°F. (100°C.).

The aluminum soaps are generally prepared by the precipitation process which yields a product in the form of a powder. In this process, a sodium or other alkali metal soap is formed by neutralization of an alkanoic acid with the appropriate alkali metal hydroxide. Thereafter, the alkali metal soap is treated with an aqueous solution of a water soluble aluminum salt to precipitate the aluminum soap which is recovered as a powder after filtration and drying. The degree of neutralization is controlled by controlling the mole ratios of the water soluble soap and the water soluble aluminum salt. The commercial aluminum soaps usually contain upto about 0.5% water and small amounts of free alkanoic acids as impurities.

The water soluble foaming, non-cationic, organic detergents which can be used in the detergent compositions of this invention include anionic, amphoteric, nonionic, polar nonionic and zwitterionic detergents and mixtures thereof. This ingredient can suitably comprise about 5 to about 50% by weight of the total composition.

Suitable anionic organic detergents are, for example, the water-soluble salts of sulfated or sulfonated organic reaction products having in their molecular structure and alkyl group containing from 8 to 20 carbon atoms and a sulfuric ester or sulfonic acid radical. Such surfactants include the sodium or triethanolamine alkyl sulfates, especially those derived by reduction of tallow or coconut oil glycerides; sodium or potassium alkyl benzene sulfonates, especially those in which the alkyl group contains from 9 to 15 carbon atoms; sodium alkyl glyceryl ether sulfonates, especially those ethers of higher alcohols obtained from tallow or coconut oil; sodium coconut oil fatty acid monoglyceride sulfates and sulfonates; sodium and ammonium salts of sulfuric acid esters of the reaction product of one mole of a higher alcohol and about three moles of ethylene oxide; and salts of condensation products of alkanoic acids with sarcosine or N-methyl taurine. Also suitable are the $C_{10} - C_{20}$ alkane sulfonates and the $C_{12} - C_{20}$ olefin sulfonates.

Conventional soaps are also operable anionic detergents for the purposes of this invention. Suitable soaps include the sodium, potassium and lower alkanolamine salts of fatty acids occurring in coconut oil or tallow as well as salts of synthetically produced alkanoic acids.

Preferably, anionic organic detergents of the high sudsing type are used for the hair cleansing compositions of this invention. Thus, alkyl sulfates, water soluble soaps and alkyl ether ethylene oxide sulfates as described above are used to special advantage. These and the foregoing anionic detergents can be used in the form of their sodium, potassium, ammonium and lower alkanolamine salts. The lower alkanolamines each have from 1 to 3 carbon atoms, such as triethanolamine.

Suitable amphoteric detergents include the long chain imidazoline derivatives having the general formula

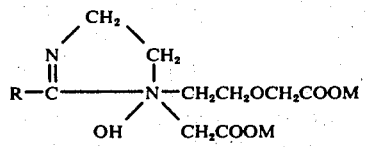

the alkyl beta-amino propionates, $RCN(C_2H_4COOM)(H)$, and the beta alkyl imino dipropionates, $RCN(C_2H_4COOM)_2$. In each of the foregoing formulas, R is an alkyl group of 7 to 17 carbon atoms and M is a cation to neutralize the charge of the anion, for example, sodium, potassium, ammonium and alkanolammonium. A preferred amphoteric detergent is 2-C12 alkyl, 1-hydroxy, 1-ethoxyethanoic acid, 1-ethanoic acid imidazoline, disodium salt.

Suitable zwitterionic detergents are the betaines and sulfobetaines such as alkyl dimethyl ammonio acetates and alkyl dimethl ammonio propane sulfonates wherein the alkyl radical contains 12 to 18 carbon atoms. Many examples of these detergents are set forth in Canadian Pat. No. 696,355.

Suitable polar nonionic surfactants for use in the inventive compositions are the amine oxides of the general formula $R_1R_2R_3N \rightarrow 0$ wherein $R_1$ is an alkyl, alkenyl, or mono-hydroxy alkyl radical having from 10 to 16 carbon atoms, and $R_2$ and $R_3$ are each $C_1 - C_3$ alkyl or hydroxyalkyl. A preferred amine oxide is dodecyl dimethyl amine oxide. Other operable polar nonionic detergents are the phosphine oxides having the general formula $R_1R_2R_3P \rightarrow 0$ wherein $R_1$, $R_2$ and $R_3$ have the same meanings as the corresponding radicals in the amine oxide formula. A preferred phosphine oxide is dodecyl dimethyl phosphine oxide.

Although nonionic detergents are not preferred for the detergent compositions for cleansing the hair, such detergents are used alone or in combination with anionic detergents in compositions for cleansing textiles. The nonionic detergents may be described as compounds produced by the condensation of ethylene oxide groups with an organic hydrophobic compound, which may be aliphatic or alkyl aromatic in nature. As those skilled in the art are well aware, the length of the hydrophilic or polyethenoxy radical for condensation with any particular hydrophobic group can be readily adjusted to yield a water soluble compound having the desired degree of balance between hydrophilic and hydrophobic elements.

The satisfactory nonionics include the condensation product of aliphatic alcohols having from 8 to 18 carbon atoms, either straight or branched chain, with 5 to 30 moles of ethylene oxide. Also suitable are the polyethylene oxide condensates of alkyl phenols having 6 to 12 carbon atoms in the alkyl group and about 5 to 30 ethylene oxide groups. Further suitable nonionic detergents are those compounds formed by condensing ethylene oxide with a hydrophobic base formed by the condensation of propylene oxide with propylene glycol. The molecular weight of the hydrophobic portion may range from about 900 to 4000 and the percentage of ethylene oxide may range from 20 to 80% of the weight of the condensate. Liquid products are obtained up to the point where the polyoxyethylene content is about 50% of the condensation product.

Preferred detergent compositions which are especially adapted to cleansing the hair and scalp comprise an aqueous medium containing up to 15% by weight, preferably 2 to 10% by weight, of a $C_2 - C_3$ alkanol, 10 to 40% by weight of a $C_{10} - C_{16}$ alkyl sulfate detergent with either a water soluble soap or an amphoteric imidazoline detergent and from 1% to 5% by weight of an aluminum soap. In the detergent mixtures the alkyl sulfate detergent is generally present in a minor proportion of the mixture. The alkanols include ethanol, propanol, isopropanol, propylene glycol and glycerine. These preferred compositions cleanse and condition the hair and result in a reduction in the time required for the wet hair to dry.

Because the aluminum soap is not soluble in the preferred hair cleansing compositions and has a tendency to separate from the aqueous medium, it is advantageous to include about 0.1 to 3%, preferably 0.3 to 2%, by weight of a waxy material in the compositions to facilitate suspension of the aluminum soap. Suitable waxy materials include the naturally occurring waxes and synthetic waxes having a melting point of at least 110°F. (43°C.) and preferably 120°F. (49°C.). The naturally occurring waxes consist essentially of esters of monohydric, high molecular weight alcohols, including sterols, and higher fatty acids. The natural waxes include carnauba, candelilla, montan and bees' waxes. The synthetic waxes are similar in appearance and physical properties (not chemically) to the natural waxes and include hydrogenated fats and certain higher alcohols and amides. Among the suitable synthetic waxes are hydrogenated castor oil, stearyl amide, stearyl alcohol, cetyl alcohol, stearyl monoethanolamide, and the monoethanolamide of castor oil. However, the naturally occurring waxes are the preferred suspending materials, with carnauba wax being optimum.

In addition to the foregoing components, the detergent compositions for the hair may include the usual adjuvants found in shampoo compositions. Among the usual adjuvants are the $C_8 - C_{18}$ fatty acid alkanolamide foam boosters such as lauric monoethanolamide and lauric-myristic diethanolamide; the gums such as carboxymethylcellulose and hydroxypropyl cellulose; perfumes; sequestering agents such as tetra-sodium ethylene diamine tetraacetate and inorganic phosphate; and buffers such as citric acid and borates. Preservatives such as formaldehyde and benzoate also may be present. With the exception of the alkanolamides which may be present in amounts from about 1 to 8% by weight of the total composition, such adjuvants usually are present in amounts from about 0.05 to about 2% by weight.

Preferred detergent compositions for cleansing soiled natural and synthetic fibrous materials such as cotton, wool, nylon, acetate and dacron are solid paticulate compositions comprising about 5 to 50% by weight of an anionic sulfated or sulfonated detergent or an ethoxylated nonionic detergent or a mixture thereof; about 2.5 to 50% by weight of the aluminum soap, the weight ratio of detergent to soap being in the range of 5:1 to 1:3, and the balance being a water-soluble inorganic or organic builder salt, the weight ratio of builder to detergent being from about 10:1 to about 1:1. Suitable inorganic builder salts are the water soluble alkaline and neutral builder salts such as the sodium and potassium phosphates, silicates, carbonates, borates and sulfates. preferred inorganic builders are sodium tripolyphosphate and sodium pyrophosphate. Suitable organic builders are sodium and potassium nitrilotriacetate, ethylene diamine tetraacetate, citrate, polymeric polycarboxylates, polymeric polysulfonates, and the like. Such builders and their equivalents are well known to those skilled in the detergent art.

The textile cleansing compositions may also include the standard adjuvant materials commonly found in such compositions. The usual adjuvants include perfumes; corrosion inhibitors such as melamine; preservatives; antiseptic agents; anti-redeposition agents such as sodium carboxymethyl cellulose; and optical whiteners. Each adjuvant is present in an amount of less than about 2% by weight, preferably in an amount in the range of 0.05 to about 1% by weight.

Typically the cleansing compositions are prepared by spray drying or drum drying an aqueous slurry of the detergent composition. Alternatively, particulate mixtures can be prepared by an agglomeration process. Such processes result in a product which contains water as an additional component in an amount of about 2 to 15% by weight.

The following specific examples are further illustrative of the nature of the present invention and it is to be understood that the invention is not limited thereto. All ingredients are set forth as a percentage of the total composition unless otherwise indicated.

EXAMPLE I

A detergent composition for cleansing the hair and scalp is prepared having the following formula.

|  | % by weight |
|---|---|
| Potassium soap (mixture of 50% coconut soap, 27.5% tallow soap and 22.5% oleate soap) | 30.0 |
| Triethanolamine lauryl sulfate | 1.6 |
| Aluminum stearate* | 3.0 |
| Isopropyl alcohol (92.5%) | 4.0 |
| Carnauba wax | 0.5 |
| Water, perfume, color | balance |
|  | 100.0 |

*

The foregoing composition is prepared by heating a 60% aqueous mixture of the potassium soap to a temperature of about 130° to 150°F. (54° to 65°C.) and then adding a 40% aqueous solution of the triethanolamine lauryl sulfate with agitation. Melted carnauba wax is then added to the aqueous surfactant solution with agitation. After the wax is dispersed, the balance of the water is added and the mixture is cooled with agitation to a temperature of about 120° to about 130°F. (49° to 54°C.) where a mixture of aluminum stearate and isopropyl alcohol is added. The resultant mixture is further cooled to 80° to 100°F. (27° to 38°C.) with agitation and the perfume is added. A white, opaque liquid lotion is achieved.

This lotion product provides good cleansing and hair conditioning effects and also reduces the time required for the drying of the wet hair. The faster drying is illustrated in a laboratory comparison with a leading commercial shampoo containing an anionic alkyl sulfate as the principal detergent. In this comparative test, four hair bundles weighing approximately 5 grams each are shampooed twice with 3 milliliters of shampoo diluted with about four parts of water at about 105°F. (40°C.) for about 40 seconds. After the second shampooing, the bundles are rinsed for 30 seconds with water at about 100°F. (38°C.) and lightly toweled. Each bundle is weighed to provide a wet weight and the difference between the wet weight and the dry weight represents the moisture which must evaporate or be removed by brushing. Each hair bundle receives 10 brush strokes with a conventional, nylon-bristled, hair brush at 5 minute intervals and the weights of the bundles are recorded at 10 minute intervals for 2 hours. The results are shown in Table A below:

Table A

| Drying Time(min.) | % Water Loss* | |
|---|---|---|
| | Example I | Commercial Shampoo |
| 20 | 23.7 | 16.4 |
| 30 | 26.6 | 26.3 |
| 60 | 45.8 | 44.0 |
| 90 | 58.2 | 55.7 |
| 120 | 65.8 | 63.9 |

*% Water Loss equals the sample weight minus the dry weight divided by the wet weight minus the dry weight, all times 100%

The laboratory test results are confirmed by evaluations in the beauty shop using the half head technique. In this test, one-half of the head is covered with plastic and the other half of the head is shampooed twice with 10 grams of the subject's favorite brand of shampoo for 2 – 3 minutes and rinsed with 105°F. (40°C.) water after each shampooing until the foam disappears in the rinse water. Excess water is removed from the rinsed hair by the beautician by squeezing the hair between the fingers as the hand is moved from the scalp to the ends of the hair. The plastic cover is then placed over the shampooed hair and the other half of the head is shampooed with the exemplified composition, rinsed and squeezed in similar fashion. After the shampooings are complete, the hair is patted with a cotton towel for 1 to 2 minutes and each side of the head is brushed for 10 strokes with a cushion brush having nylon bristles and the brushings are repeated at 5 minute intervals. Identical hair brushes are used for each side of head and the brushings are alternated so that opposite sides of the head are brushed first to eliminate any bias. After each brushing, the subject rates each side of the head for dryness according to a scale from 0 to 10 where 0 represents the wet hair and 10 represents dry hair according to the subject. When the inventive composition is compared with a leading commercial baby shampoo as the favorite brand in such a test, 11 out of 12 subjects with medium to long hair found that hair shampooed with the inventive composition dried faster.

EXAMPLES II AND III

The composition of Example I is repeated with the exception that 3% by weight of aluminum oleate and aluminum ricinoleate respectively are substituted for aluminum stearate. The resultant compositions are opaque lotions which are stable and effective in cleansing the hair while decreasing the time required for drying the wet hair.

EXAMPLE IV

A hair cleansing composition having the following formula is prepared according to the procedure for Example I.

| | % by weight |
|---|---|
| Disodium salt of 2-lauryl, 1-hydroxy, 1-ethoxyethanoic acid, 1-ethanoic acid imidazoline | 8.0 |
| Triethanolamine lauryl sulfate | 1.6 |
| Aluminum stearate* | 3.0 |
| Isopropyl alcohol (92.5%) | 4.0 |
| Carnauba wax | 0.5 |
| Water, perfume | Balance |
| | 100.0 |

The foregoing shampoo is an opaque lotion which cleans effectively and simultaneously conditions the hair, Further, this hair cleansing composition speeds the rate of drying of the wet, shampooed hair when tested in the laboratory and the beauty shop in the manner described in Example I above.

Equivalent fast drying results are obtained when 1%, 2%, 4% and 5% of aluminum stearate is substituted for the 3% concentration in the formulation of Example IV, with somewhat faster drying at the higher concentrations and slightly slower drying at the 1% concentration.

EXAMPLE V

The composition of Example IV is repeated with the exception that 2% by weight of sodium stearate soap is substituted for 2% of water in the formulation. The resultant shampoo improves the rate of drying of the wet, shampooed hair when tested according to the procedures set forth in Example I and provides slightly enhanced conditioning effects on the dry hair.

EXAMPLES VI AND VII

The composition of Example IV is repeated with the exception that 15% by weight of sodium N-lauryl beta-amino propionate and 15% by weight of ammonium lauryl triethenoxy ether respectively is substituted for the combination of imidazoline detergent, lauryl sulfate detergent and 5.4% by weight of water. Again, lotion shampoos characterized by fast wet hair drying characteristics are produced.

EXAMPLE VIII

The following shampoo composition is produced according to the procedure of Example I.

| | % by weight |
|---|---|
| Triethanolamine lauryl sulfate | 19.0 |
| Lauric monoethanolamide | 5.0 |
| Aluminum stearate* | 5.0 |
| Ethanol | 6.0 |
| Carnauba wax | 2.0 |
| Water, perfume | balance |
| | 100.0 |

This shampoo is characterized by good cleansing in hard and soft water and improved dry hair manageability and luster in addition to a faster wet hair drying rate.

EXAMPLE IX

The following textile cleansing composition is prepared in particulate form.

|  | % by weight |
|---|---|
| Sodium lauryl sulfate | 20.0 |
| Aluminum stearate* | 40.0 |
| Sodium sulfate | 40.0 |
|  | 100.0 |

When this particulate composition is added to a top-loading automatic washing machine in an amount of 117 grams to launder cotton terrycloth towels, it is noted that the wet towels dry more quickly.

EXAMPLES X AND XI

The following two spray dried particulate textile cleaning compositions are effective for cleansing soiled textiles of cotton, nylon and acetate and reducing the time required for drying of the wet textiles.

|  | % by weight | |
|---|---|---|
|  | X | XI |
| Sodium dodecyl benzene sulfonate | 18.0 |  |
| Ethoxylated $C_{12}$-$C_{14}$ alcohol (10 EtO) |  | 10.0 |
| Sodium stearate |  | 3.0 |
| Aluminum stearate* | 15.0 | 5.0 |
| Sodium tripolyphosphate | 35.0 | 10.0 |
| Sodium nitrilotriacetate |  | 25.0 |
| Sodium silicate (1 $Na_2O$:2.3 $SiO_2$) | 5.0 | 5.0 |
| Sodium sulfate | 19.0 | 36.0 |
| Water | 8.0 | 6.0 |
|  | 100.0 | 100.0 |

Also within the scope of the present invention is the method of decreasing the time required for drying of cleansed wet hair and cleansed wet textiles which comprises the steps of contacting the hair or textiles with an aqueous bath containing a detersive proportion of a water soluble, foaming, non-cationic, organic detergent in the presence of an aluminum $C_{12}$ – $C_{18}$ soap, the weight ratio of detergent to soap being from 40:1 to 1:4, rinsing the cleansed substrate with water, and drying the cleansed substrate.

What is claimed is:

1. A detergent composition for cleansing and conditioning the hair which is characterized by a faster drying rate for the wet cleansed hair consisting essentially of a cleansing proportion of a water soluble, foaming non-cationic, organic detergent selected from the class consisting of anionic, amphoteric, polar nonionic and zwitterionic detergents and mixtures thereof, an aluminum soap containing 12 to 18 carbon atoms, a wax selected from the class consisting of naturally-occuring and synthetic waxes having a melting point of at least 120°F and an aqueous medium wherein said detergent is present in an amount of about 10 to about 40% by weight, said soap is present in an amount of about 0.5 to about 10% by weight, said wax is present in an amount of about 0.1 to about 3.0% by weight and the balance is said aqueous medium containing from 0 to 15% by weight of a $C_2$–$C_3$ alkanol, the weight ratio of detergent to aluminum soap being no greater than 40:1.

2. A detergent composition according to claim 1 wherein said aluminum soap is selected from the group consisting of stearate, oleate, ricinoleate and mixtures thereof.

3. A detergent composition according to claim 1 wherein said wax is a naturally occurring wax selected from the group consisting of carnauba, candelilla, montan and bees wax.

4. A detergent composition according to claim 3 wherein said detergent is selected from the group consisting of anionic and amphoteric detergents and mixtures thereof and is present in an amount of 10 to 40% by weight, said aluminum soap contains from 16 to 18 carbon atoms and is present in an amount of about 1 to 5% by weight and said alkanol is present in an amount of 2 to 10% by weight.

5. A detergent composition according to claim 4 wherein said organic detergent is a mixture of $C_8$ – $C_{18}$ alkyl sulfate and $C_8$ – $C_{18}$ soap, with the solubilizing cation of the soap and the detergent being selected from he group consisting of sodium, potassium, ammonium and mono-, di-, or triethanolammonium and said wax is carnauba wax.

6. A detergent composition according to claim 4 wherein said organic detergent is a mixture of $C_8$ – $C_{18}$ alkyl sulfate and $C_7$ – $C_{17}$ alkyl imidazoline, with the solubilizing cation of the detergents being selected from the group consisting of sodium, potassium, ammonium and mono-, di- or triethanolammonium and said wax is carnauba wax.

7. The detergent composition of claim 1 wherein the weight ratio of detergent to aluminum soap is from about 15:1 to about 4:1.

8. A method of decreasing the time required for drying of cleansed wet hair which comprises the steps of contacting the hair with an aqueous bath containing a detersive portion of a water soluble, foaming, non-cationic, organic detergent selected from the class consisting of anionic, amphoteric, polar nonionic and zwitterionic detergents and mixtures thereof, and an aluminum soap containing 12 to 18 carbon atoms, wherein said detergent is present in an amount of about 10 to about 40% by weight, said soap is present in an amount of about 0.5 to about 10% by weight and the balance is an aqueous medium containing from 0 to 15% by weight of a $C_2$ – $C_3$ alkanol, the weight ratio of detergent to soap being no greater than 40:1, rinsing the cleansed hair with water, and drying the cleansed hair.

* * * * *